United States Patent [19]
Folkers et al.

[11] 3,944,659
[45] Mar. 16, 1976

[54] FOLLICULOTROPIN RELEASING HORMONE

[76] Inventors: Karl Folkers, 6406 Mesa Drive, Austin, Tex. 78731; Karl Nils Gunnar Johansson, 2215 S. Lakeshore Blvd., Austin, Tex. 78741; Bruce L. Currie, 8304 Kromer, Austin, Tex. 78758

[22] Filed: Dec. 13, 1972

[21] Appl. No.: 314,750

[52] U.S. Cl. .................. 424/1; 424/95; 23/230 B
[51] Int. Cl. .................. A61k 27/04; A61k 17/08
[58] Field of Search ........... 424/95, 1, 108, 109; 23/230 B

[56] References Cited
OTHER PUBLICATIONS

Sievertsson et al., Biochemical and Biophysical Research Communications, Vol. 44, No. 6, (1971), pp. 1566–1571.

Matsuo et al., Biochem. & Biophys. Res. Comm., Vol. 43, No. 6, (1971), pp. 1334–1339.

*Primary Examiner*—Benjamin R. Padgett
*Attorney, Agent, or Firm*—Salvatore C. Mitri

[57] ABSTRACT

A method for producing the Folliculotropin Releasing Hormone (FRH) biosynthetically is provided by utilizing, as key starting materials, fresh hypothalamic tissue, a buffered incubation medium, an ATP synthesizing system, radioactively labeled amino acids and a mixture of 21 naturally occuring amino acids. Biosynthesis of the FRH is accomplished by incubation of the hypothalamic tissue for a short period of time in the presence of all the reagents necessary to promote the biosynthetic system to produce the Folliculotropin Releasing Hormone (FRH) of the hypothalamus gland of mammals. Examples of methods to isolate the FRH free of the luteotropin releasing hormone (LRH) are provided.

4 Claims, 4 Drawing Figures

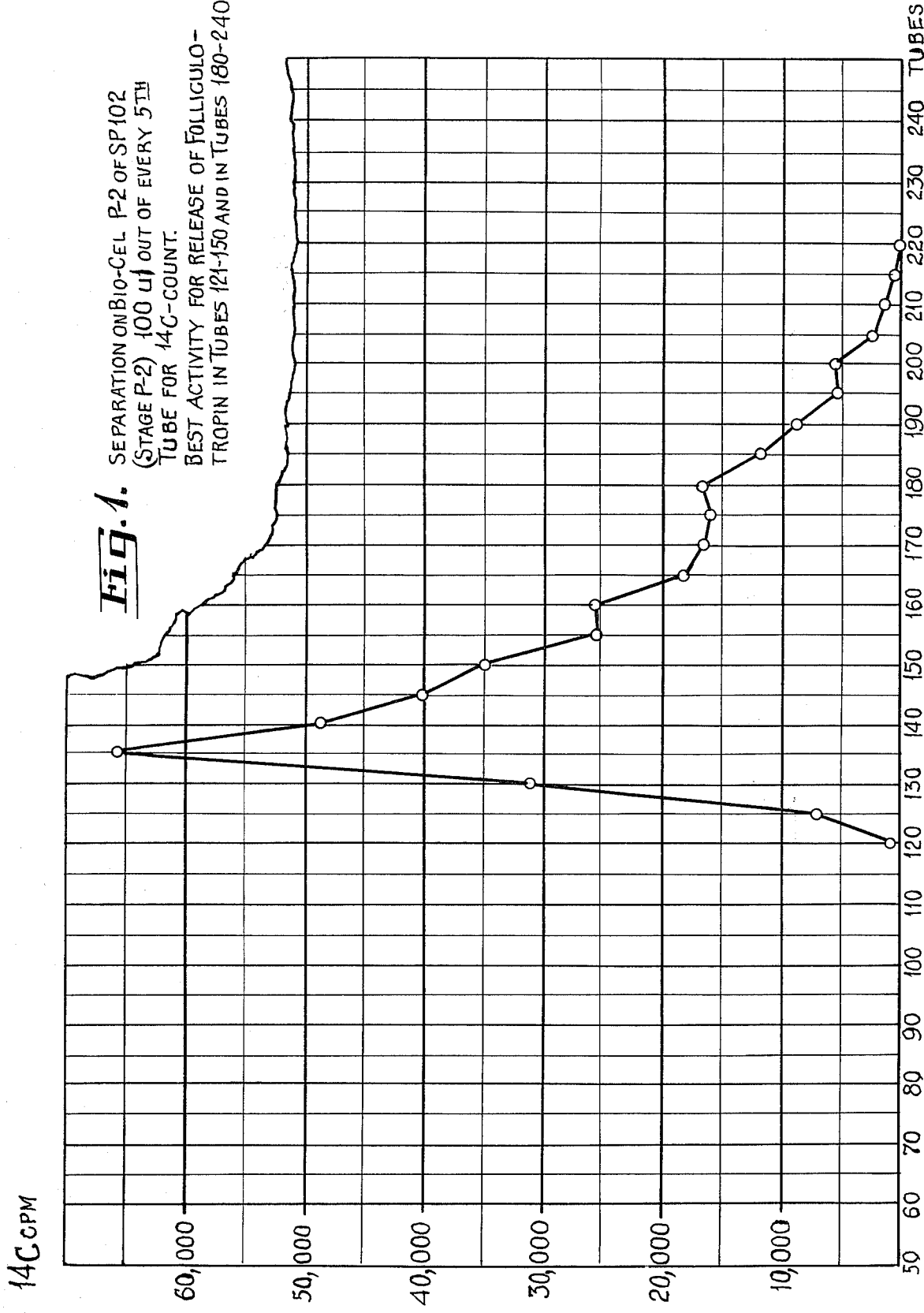

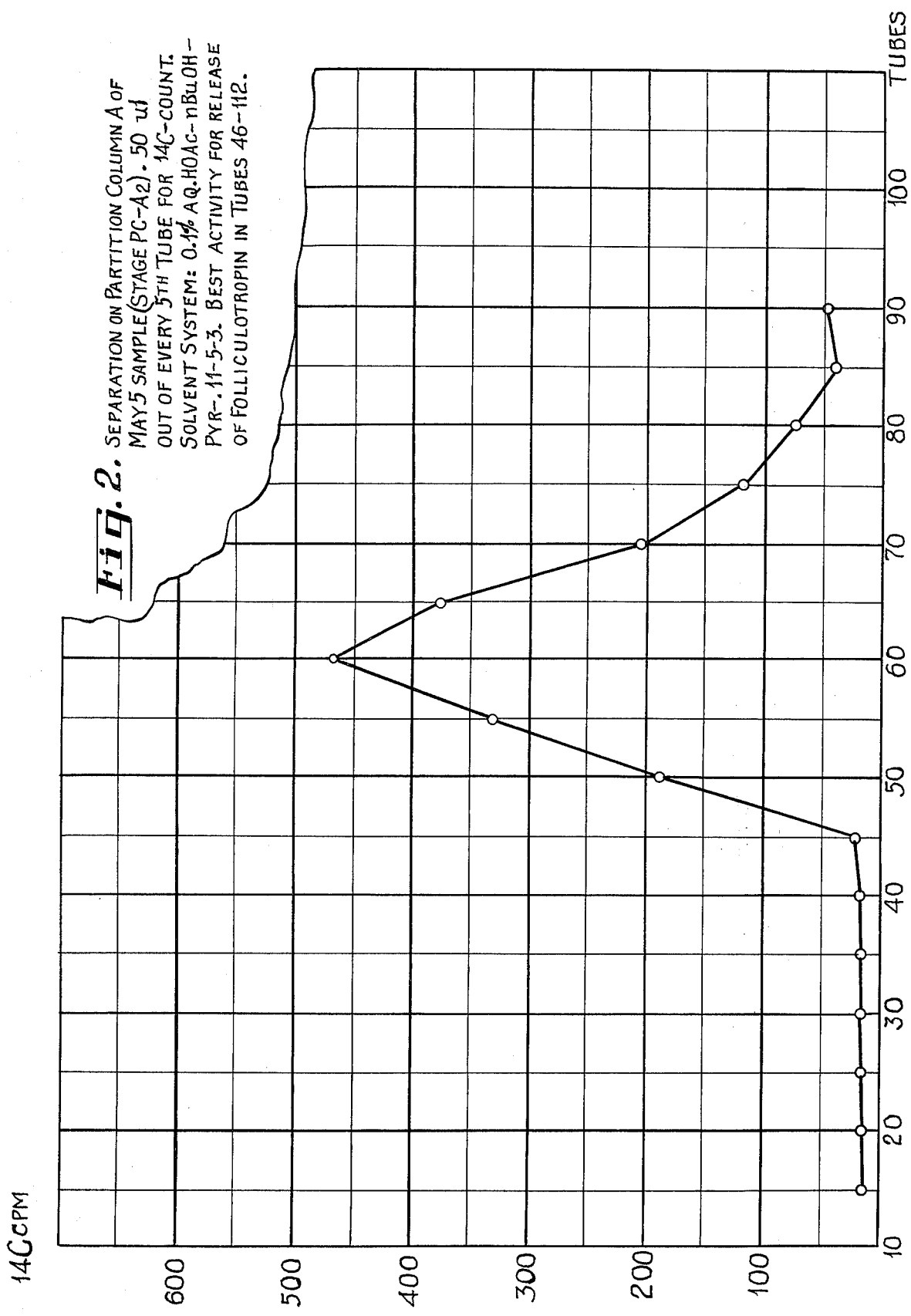

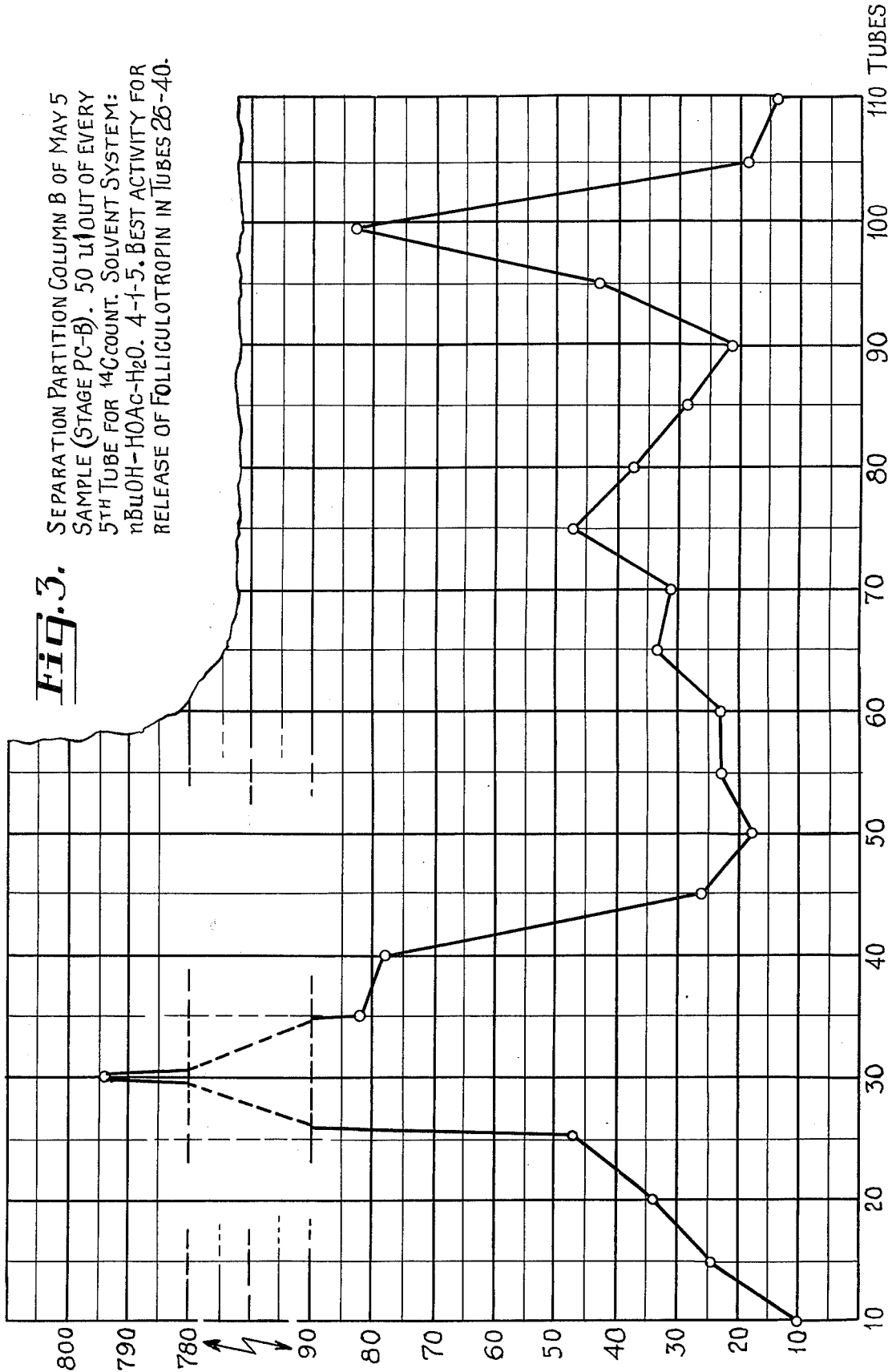

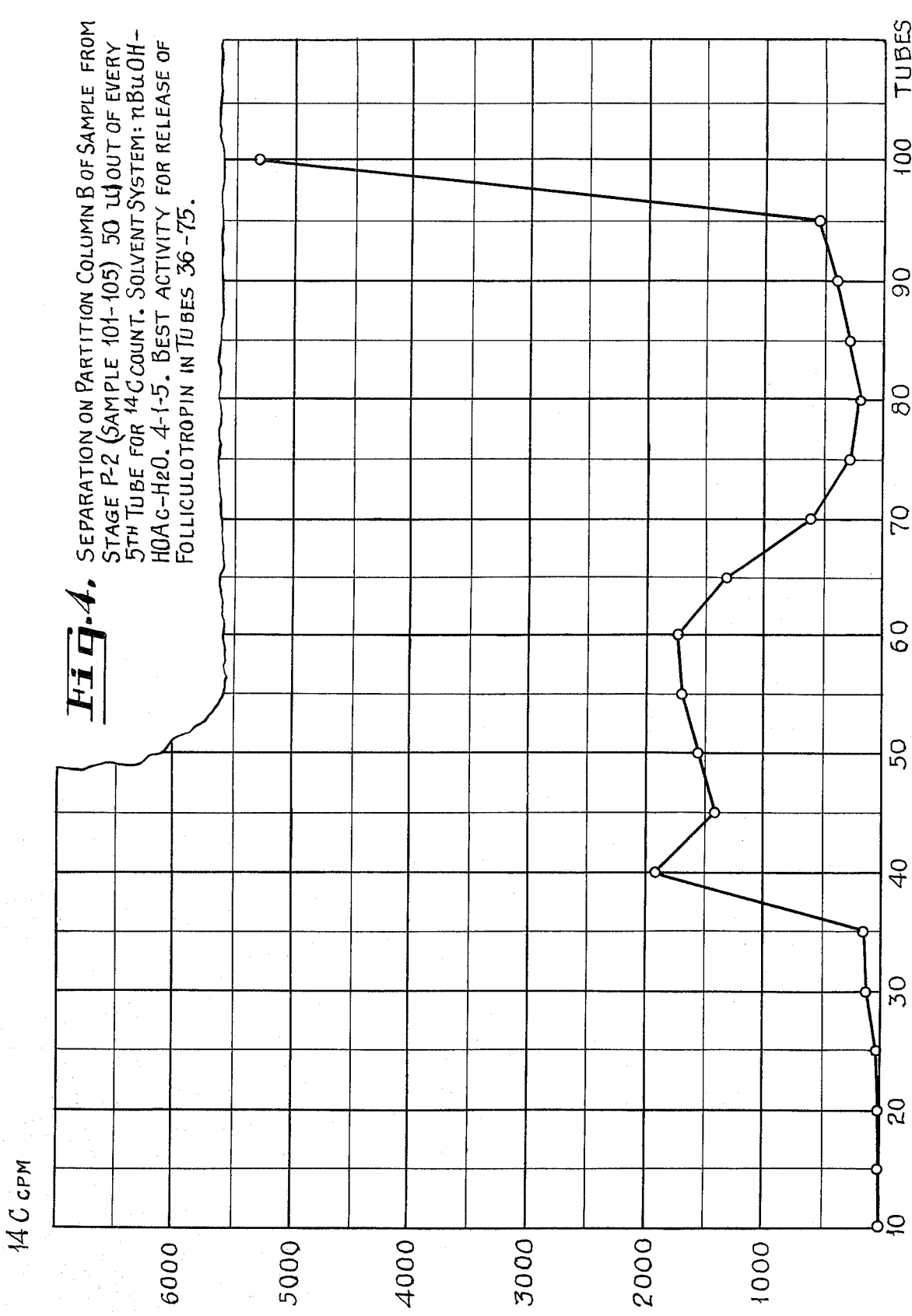

FOLLICULOTROPIN RELEASING HORMONE

This invention relates to the Folliculotropin Releasing Hormone (FRH) of the hypothalamus of mammals, and to alternative methods of biosynthesis and isolation of said FRH. This biosynthetic FRH has the biological, chemical and hormonal properties of the Folliculotropin Releasing Hormone (FRH) of the hypothalamus in the brain of mammals including man.

BACKGROUND OF THE INVENTION

A substance that stimulates the secretion of the follicle stimulating hormone has been reported by many investigators. This substance is present in homogenates of hypothalamic tissue from many species. The hypothalamus is a part of the forebrain; prosencephalon, which unlike the cerebellum and crebral hemispheres, has maintained a relative constancy of arrangement throughout its phylogenetic history. The hypothalamus is a small section of tissue of the diencephalon which is the posterior part of the prosencephalon, consisting of the hypothalamus, thalamus, metathalamus, and epithalamus. The hypothalamus is not considered as an organ with boundaries, but rather as a region of brain tissue which has significant functions in many aspects of mammalian physiology. Basically, the hypothalamus is divisible into medial and lateral portions. The medial portion joins the third ventricle. The lateral portion contains cells that are diffusely arranged among the fibers of what has long been called the medial forebrain bundle. An anatomic relationship which is a constant feature of the hypothalamus is its intimate association with the pituitary gland. The pituitary or hypophysis consists of anterior and posterior lobes, and the pars intermedia. Biochemical transport of the neurohormones from the hypothalamus to the anterior lobe or adenohypophysis is provided by certain blood vessels in a portal system which is a network of capillaries. The blood in these capillaries passes down the pituitary stalk and becomes distributed through another system of capillaries in the anterior lobe and one of the neurohormones thus transported is folliculotropin releasing hormone (FRH).

It is generally considered that there is one hypothalamic releasing hormone for each anterior pituitary hormone. This concept has not been proven and it has been found that the known luteotropin releasing hormone (LRH) and thyrotropin releasing hormone (TRH) stimulate the release of two pituitary hormones. It has been found that TRH can stimulate the release of prolactin and thyrotropin and that LRH can stimulate the release of luteotropin and folliculotropin.

A prolactin releasing hormone (PRH) has recently been described as being chemically distinct from TRH. [Valverde-R., et al., *Endocrinology*, 91, 982 (1972)]. We now describe the biosynthesis of a Folliculotropin Releasing Hormone (FRH) chemically separable from LRH.

It has been proposed by Schally and White [Schally, et al., Science, 173, 1036 (1971) and White, *Hypophysiotropic Hormones of the Hypothalamus*, J. Meites, ed., p. 248, 1970] that luteotropin releasing hormone (LRH) is the natural regulator of both luteotropin and folliculotropin. More recently, [Guillemin and Burgus, *Scientific American*, 227, 24 (1972)] it has been stated by noted investigators that "A third gonadotropic hormone, FSH (follicle stimulating hormone), may have its own hypothalamic releasing factor, FRF, but that has not been demonstrated."

We have found, indeed, that LRH releases folliculotropin to a limited degree in addition to a potent release of luteotropin. More important is our finding that hypothalamic extracts contain a hormone, chemically distinct from LRH, that stimulates a very high level of folliculotropin release as well as a limited release of luteotropin. The functions of the gonads are thus controlled by two hypothalamic releasing hormones, LRH and FRH, that both regulate the release of luteotropin and folliculotropin from the anterior pituitary. Each releasing hormone appears to have a primary and a secondary regulatory activity.

Only a few nanograms of each releasing hormone appears to exist in the hypothalamus of a single animal. Therefore, hypothalami from thousands of animals are required to isolate a sufficient quantity for structure elucidation studies. The biosynthetic approach to the isolation of a new hormone makes it possible to attach a radioactive tag to the compound of interest and increase the amount of hormone present in the starting tissue. Once the hypothalamic hormone has been radioactively labeled, it can be added to a large amount of tissue. This process increases the total quantity of hormone present to a quantity suitable for structure elucidation after the necessary purification procedures.

THE INVENTION

It has been found now that the folliculotropin releasing hormone (FRH) is chemically distinct from other releasing hormones present in hypothalamic extracts. The folliculotropin releasing hormone can be biosynthesized and radioactively labeled by a process involving incubation of fresh hypothalamic tissue in the presence of a radioactive amino acid.

The folliculotropin releasing hormone (FRH) activity present in hypothalamic extracts has become discernable since the structure elucidation [Matsuo, et al. *Biochem. Biophys. Res. Commun.*, 43, 1334 (1971)) and synthesis (Sievertsson, et al., *Biochem. Biophys. Res. Commun.*, 44, 1566 (1971) and others] of the luteotropin releasing hormone (LRH).

Through careful study of the behavior of synthetic LRH in numerous biological test systems, it has been shown that LRH can stimulate the release of luteotropin and folliculotropin. Synthetic LRH will not release, in vitro, more than 35,000 ng/ml of FSH even at dose levels up to 500 ng/ml. A dose of 0.9 ng and 500 ng have similar releasing activity for folliculotropin. Our partially purified hypothalamic extracts at Stage SP have shown extremely potent Folliculotropin Releasing Activity (FRH). Dose levels as low as 0.2 hypothalamic fragment equivalent (h.f.e.) from some preparations released > 128,000 ng FSH/ml in the in vitro assay procedure. Folliculotropin Releasing Hormone (FRH) activity can be separated from Luteotropin Releasing Hormone (LRH) activity by chromatographic procedures described in greater detail herein below. For example:

Incubated tissue is lyophilized, extracted and defatted to give a standard preparation (Stage SP). Stage SP material is twice passed through Bio-Gel P-2 (Stage P-2) and then chromatographed on a Sephadex partition column in solvent system A. After this procedure the LRH and FRH activities are separated. A second chromatography in the same system gave a good separation of areas corresponding to the known LRH and the previously unknown FRH.

Alternatively, Stage P-2 Folliculotropin Releasing Hormone (FRH) material was chromatographed on a Sephadex partition column in solvent system B. The PC-B FRH was then chromatographed on diethylaminoethyl-Sephadex. The LRH and FRH present are cleanly separated, LRH is unretained and FRH is eluted with 500mM NH₄OAc after a continuous or stepwise gradient.

Alternatively, Stage PC-B FRH was chromatographed on carboxymethyl-Sephadex. The FRH active material is unretained and the LRH active material is eluted with 100 mM NH₄OAc after a stepwise gradient.

Alternatively, Stage PC-A Folliculotropin Releasing Hormone (FRH) was chromatographed on carboxymethyl-Sephadex. The FRH present was unretained and the LRH remaining was eluted with 100 mM NH₄OAc after a stepwise gradient.

Alternatively, Stage PC-A Folliculotropin Releasing Hormone (FRH) was chromatographed on carboxymethylcellulose. The FRH present was unretained and the LRH present was eluted with 70 mM NH₄OAc during a continuous gradient from 2 mM to 100 mM NH₄OAc.

Alternatively, PC-A FRH and LRH was chromatographed on diethylaminoethyl-Sephadex. The LRH material present is unretained and the Folliculotropin Releasing Hormone (FRH) is eluted with 500 mM NH₄OAc after a continuous or stepwise gradient from 2 mM to 500 mM.

The above described procedures produce biosynthetic Folliculotropin Releasing Hormone (FRH) free from the known decapeptide hormone LRH. The biosynthetic FRH of this invention is readily obtained by these procedures and is radioactively labeled with $^{14}$C for ease of identification and as an aid to the purification procedures.

Folliculotropin Releasing Hormone (FRH) is an important regulator of gonadal function in mammalian species. It could be used separately or in conjunction with the decapeptide LRH. In many respects, FRH may be more important to fertility control than LRH.

The examples given below are provided to exemplify the invention, and modification of these examples in terms of the sequential uses of the purification steps, as well as the selection of experimental conditions as to incubation time, temperature, solvents, column sizes, adsorbents, and other experimental details are all considered in the scope of the invention. While all of these alternatives are successful, in principle, some of the alternatives are more practical for isolation purposes than others.

The following examples are presented to illustrate methods of carrying out the present invention, and it should be understood that incubation medium reagents, radioactively labeled amino acids, column dimensions and chromatographic systems are only illustrative and are not intended to be limitative of the possible means available to produce radioactively labeled biosynthetic Folliculotropin Releasing Hormone (FRH). Additional available buffered incubation media which fall within the scope of this invention incude, but are not limited to such buffers as citrate, acetate, formate, carbonate-bicarbonate, Trishydrochloride. Radioactive labeled amino acids include, but are not limited to tritium ($^3$H) and carbon-14 ($^{14}$C) substitution at any position and any specific activity commercially available that can be incorporated by the hypothalamic tissue into Folliculotropin Releasing Hormone (FRH). Gel filtration materials available include, but are not limited to such gels as Sephadex G-10, G-15 and G-25; and Bio-Gel P-2 and P-4. Partition chromatography supports include, but are not limited to Sephadex G-25 Fine, Bio-Gel P-2 (200-400 mesh) and Sephadex LH-20. Ion exchange chromatographic supports include, but are not limited to such supports as carboxymethylcellulose (CMC), diethylaminoethylcellulose (DEAE-C), carboxymethyl-Sephadex (CM-S), diethylaminoethyl-Sephadex (DEAE-S), sulfoethyl-Sephadex (SE-S), sulfopropyl-Sephadex (SP-S), diethyl-(2-hydroxy-propyl) aminoethyl-Sephadex (QAE-S), carboxymethyl-Bio-Gel (CM-BG) and BioRad AG-11A8 Ion Retardation resin (BG-AG).

Results of radioactive distribution are graphically represented in the figures of the accompanying drawing wherein:

FIG. 1 is a graph illustrating the distribution obtained from separation on Bio-Gel P-2 of SP 102;

FIG. 2 is a graph illustrating the distribution obtained from separation on partition on column A of Stage PC-A₂ samples;

FIG. 3 is a graph illustrating the distribution obtained from separation on column B of Stage PC-B samples; and, FIG. 4 is a graph illustrating the distribution obtained from separation on partition column B of Stage P-2 samples.

EXPERIMENTAL PROCEDURES

THE BIOSYNTHESIS AND ISOLATION OF THE FOLLICULOTROPIN RELEASING HORMONE (FRH)

SECTION A. The biosynthesis of the Folliculotropin Releasing Hormone (FRH).

CHART I; EXAMPLE I

Incubation of Porcine Hypothalamic Fragments to Produce Biosynthetic Folliculotropin Releasing Hormone (FRH)

Porcine hypothalamic fragments were collected at Hormel and Co. slaughterhouse, Austin, Minnesota. They were placed in a Nalgene bottle in batches of 500 fragments and packed in wet ice in a styrofoam box and sent by Air Mail to the Institute for Biomedical Research, Austin, Texas. The ice cold tissue was received the day following shipment. About 25 shipments have been received and incubated. The weight of 500 fragments ranged from 213 g to 372 g.

Each batch of 500 hypothalamic fragments was homogenized and incubated in 500 ml of a medium containing 20 mM potassium phosphate, pH 7.4, 150 mM mannitol, 8 mM MgCl, 80 mM KCl, 0.2 mM EDTA, 10 mM sodium-succinate, 1 mM ADP, amino acid mixture 0.25 mM in each amino acid, 50 $\mu$C $^{14}$C-glutamic acid (UL, specific activity 260 mC/mmole) and 50 $\mu$C $^{14}$C-glutamine (UL, specific activity 10 mC/mmole). The amino acid mixture contained Arg-, His-, Leu-, Ile-, Lys.HCl, Met-, Phe-, Thr-, Trp-, Val-, Ala-, Asp-, Asn-, Glu-, Gln-, Gly-, Hyp-, Pro-, Ser-, Tyr- and Cys.HCl. Incubation was performed for 4 hours at 32°C under an atmosphere of 95% air and 5% carbondioxide. After 4 hours the incubation mixture was frozen and lyophilized. The dry, lyophilized, incubated tissue was stored in a freezer until it was extracted.

Extraction of Biosynthetic Folliculotropin Releasing Hormone (FRH) (Stage SP)

Four lyophilized batches of incubated tissue, equivalent to 2,000 fragments were combined for extraction of the biosynthetic Folliculotropin Releasing Hormone. In a few cases, the extraction was made on 1,000 or 500 fragment equivalents. In these cases the volumes of the solvents used were one-half and one-fourth respectively of that used for extraction of 2,000 fragment equivalents.

The 2,000 fragment equivalents were suspended in 1,100 ml cold 15% methanolic acetic acid, and homogenized for 2 minutes in a 1 gallon stainless steel Waring blender. The homogenate was transferred to a 3 liter Erlenmeyer flask and the blender was rinsed twice with 100 ml of methanolic acetic acid. The homogenate was kept at room temperature for 4 hours with occasional shaking before it was filtered under reduced pressure on a large Buchner funnel with a Whatman No. 1 filter paper. The filter cake was washed with 100 ml of methanolic acetic acid and then suspended in 500 ml of methanolic acetic acid. The suspenpion was kept at room temperature for 2 hours and then in a cold room at approximately +5°C overnight. It was refiltered and the filter cake again washed with 100 ml of 15% HOAc/MeOH.

The combined filtrates were evaporated on a vacuum pump rotary evaporator, the temperature never exceeding 20°C.

The dry residue was dissolved in 350 ml of boiling distilled water and heated at boiling temperature for about 2 minutes until a clear dark brown solution was formed. The solution was quickly cooled on ice and extracted 3 times with methylene chloride in a separatory funnel using 400, 200 and 100 ml of methylene chloride respectively. The combined methylene chloride layer was extracted with 100 ml distilled water. The combined aqueous solution was evaporated on a rotary evaporator at about 40°C for ½ hour to remove dissolved methylenechloride and then frozen and lyophilized. The lyophilized preparation was dissolved with heating in methanol. The solution was kept in a refrigerator overnight and filtered. The residue on the filter paper was washed twice with 25 ml methanol. The combined methanol filtrate was evaporated on a rotary evaporator and the residue was finally dried on a lyophilizer. This residue constitutes a standard preparation (Stanprep) of the Folliculotropin Releasing Hormone (Stage SP). The weight of five Stanpreps, each equivalent to 2000 hypothalamic fragments ranged from 29.3 g to 41.1 g. Bioassay data on several Stanpreps are in Table I.

Gel Filtration Chromatography of Folliculotropin Releasing Hormone Preparations on Bio-Gel P-2 (Stage P-2)

Each Stanprep equivalent to 2,000 hypothalamic fragments was chromatographed on Bio-Gel P-2 100–200 mesh. The gel was swollen in either 0.2 N or 1.0 N aqueous acetic acid and packed in a column 5.0 × 150 mm. The Stanprep, dissolved in about 50 ml, was applied to and eluted from the column with either 0.2 N or 1.0 N acetic acid. Fractions of 14 ml were collected. The radioactive distribution in the fractions was determined and fractions were pooled according to radioactivity, lyophilized, and bioassayed in vitro for their release of luteotropin and folliculotropin. An example of the radioactive distribution from a P-2 column is given in FIG. I. and bioassay data are recorded in Table 2. The weight of the FRH active fractions was decreased to 5–10 g, which is 15–25% of the original weight.

Fractions equivalent to 10,000 hypothalamic fragments, No. 170–300 from five P-2 separations, which showed an exceptionally high release of folliculotropin were pooled and passed over a P-2 column a second time. Again the radioactive distribution was determined and fractions were pooled and bioassayed. Bioassay data are given in Table 3. The contents of tubes 140–400 were most potent in releasing folliculotropin and were chosen for further separation. The weight of these fractions was 19.0 g, which is 11.1% of the original weight of the five Stanpreps (171.5 g).

Separation of the Activities of Biosynthetic FRH and LRH Decapeptide

Many different methods were used for the further purification of FRH and for separating its activity from that of the luteotropin releasing hormone (LRH). An example is given of a series of continuous separations of one sample which succeeded in separating the activities of these two hormones. These steps are outlined in Chart I.

Following this, the purification of FRH from other samples with the help of a diversity of separation methods will be exemplified. (Charts II and III)

Isolation of Folliculotropin Releasing Hormone Activity, Partition Chromatography on Sephadex G-25 using 0.1% HOAc/$H_2$O-nBuOH-Pyr, 11-5-3. System A. (Stage PC-$A_1$)

Sephadex G-25 fine was swollen in the lower phase of the two phase solvent system 0.1% aqueous acetic acid-nbutanol-pyridine, 11-5-3, and packed in a column 2 × 90 cm. The column was washed with about 400 ml of the upper phase before a preparation previously purified on two P-2 columns, (Stage P-2) equivalent to 1,000 h.f.e. and weighing about 3 g was applied. The sample was dissolved in a few mls of the lower phase, adsorbed into the top of the column and eluted from the column with the upper phase while 10 ml fractions were collected. The fractions were pooled and assayed both in vivo and in vitro for FRH and LRH activity as shown in Table 4 and Table 5.

The contents of tubes 11–35 was the most active in releasing LH and was used for isolating the LRH activity on a carboxymethyl cellulose (CMC) column. The contents of tubes 56–100 was used for isolating the FRH activity.

Rechromatography of Folliculotropin Releasing Hormone (FRH) on a Sephadex G-25 Partition Column System A. (Stage PC-$A_2$)

The column was prepared and the sample from tubes 56–100 (about 1g) of the previous column was rechromatographed in the same way as described above. The radioactive distribution was determined (FIG. II), the contents of the tubes were pooled based on this distribution pattern and bioassayed. (Table 6). Two separated fractions, active in release of LH and FH were obtained. The activity in tubes 11–25 corresponds to LRH and is much less than the corresponding activity from the first PC-A separation. Most of the LRH activity was removed in the first PC-A separation. The activity in tubes 46–112 is essentially unchanged compared to the bioassay activity from the first separation and the contents in these tubes were further purified as described below.

Sephadex G-25 Partition Chromatography-Solvent System B: n-Butanol-Acetic-Water, (4-1-5) (Stage PC-B)

Sephadex G-25 fine was swollen in the lower phase of the freshly prepared two phase solvent system n-butanol-acetic acid-water (4-1-5) and packed in a column 2 × 100 cm. The gel was washed with about 400 ml of the upper phase and the sample from the previous partition separation (PC-$A_2$) (tubes 46-112, about 0.75 g) was dissolved in the lower phase and put onto the top of the column. The column was eluted with the upper phase and 10 ml fractions were collected.

Again the radioactive distribution over the tubes was determined and the tubes pooled according to this distribution and bioassayed. (FIG. III and Table 7). The best activity for release of FH was found in tubes 26-40. The contents of these tubes were submitted to further purification by ion exchange chromatography on DEAE Sephadex.

Ion Exchange Chromatography of Folliculotropin Releasing Hormone on DEAE Sephadex. (Stage DEAE-S).

The diethylaminoethyl (DEAE) Sephadex was swollen overnight in 1.0 M ammonium acetate ($NH_4OAc$)pH 7, filtered under reduced pressure, extensively washed with 0.002 M $NH_4OAc$ pH 7 and packed in a column 1.5 × 30 cm. The necessary amounts of 0.002 M $NH_4OAc$, pH 7 and 0.100 M $NH_4OAc$, pH 4 were mixed to give solutions 0.010 M, 0.020 M, 0.040 M, 0.060 M and 0.080 M in $NH_4OAc$, the pH also ranging from 7 to 4.

The sample from tubes 26-40 from the previous partition chromatrographic separation (about 0.3 grams) was dissolved in 0.002 M $NH_4OAc$ and adsorbed onto the top of the column. The column was eluted with 50 ml each of the stepwise $NH_4OAc$ gradient solutions described above. Finally the column was washed with 50 ml of a solution 0.5 M in $NH_4OAc$ and 2 M in HOAc. All fractions were bioassayed for release of LH and FH. The 0.5 M $NH_4OAc$ eluate showed exceptionally good folliculotropin releasing hormone activity. (Table 8)

Isolation of the Luteotropin Releasing Hormone (LRH) Activity

The luteotropin releasing hormone which is a decapeptide has already been isolated from hypothalamic tissue and its structure has been elucidated and confirmed by synthesis. The behavior of this hormone in different chromatographic systems is known. The separation of the activity of LRH and FRH on a second partition chromatography column by use of 0.1% aqueous HOAc-n-BuOH-Pyr, 11-5-3, has been described (PC-$A_2$).

A partial purification was obtained already on the first partition chromatography column (PC-$A_1$).

The sample in tubes 11-35 from this separation was used for further isolation of the LRH activity.

Carboxymethylcellulose Chromatography

Carboxymethylcellulose was packed in a 1.5×30 cm column and equilibrated with 0.002 M $NH_4OAc$ pH 4.5. The dry sample was dissolved in the same solvent and adsorbed onto the top of the column. It was eluted off the column by use of a continuous gradient from 0.002 M $NH_4OAc$ pH 4.5 to 0.100 M $NH_4OAc$ pH 7. A fraction active for release of both LH and FH was eluted with approximately 0.07 M $NH_4OAc$ (Table 9). It has both the chromatrographic and the bioassay characteristics of the LRH decapeptide.

CHART II: EXAMPLE II

Purification of Folliculotropin Releasing Hormone (FRH) by Use of Some Different Separation Methods

SEPARATION OF FRH FREE FROM LRH

Phenol Extraction

A 2.5 g sample from the first separation on Bio-Gel P-2, dissolved in distilled water, saturated with hydrogen sulfide, was extracted with phenol as described by Schally et al. (Schally et al., Endocrinology, 78, 726 (1966)). About 0.5 g was extracted into the phenol phase. Contrary to the findings of Schally et al., the water phase had good activity for release of Folliculotropin. Table 10.

Column Chromatographic Separations

1. The sample in the water phase from the phenol extraction (about 2 g) was purified on a 0.1% aqueous HOAc-nBuOH-Pyr, 11-5-3, partition column in the same way as has been described above. Similar to what has been described above, two well separated fractions, active in release of Luteotropin and Folliculotropin were obtained Table 11. The first one in tubes 1-27 corresponds to the decapeptide, LRH, the second active fraction in tubes 56-102, releases folliculotropin and corresponds to FRH, (Stage PC-$A_1$).

2. This fraction was further chromatographed on carboxymethylcellulose by using a continuous ammonium acetate gradient, 0.002 M pH 4.5 to 0.1 M pH 7. Column size 1.5×30 cm.

A fraction very active in release of Folliculotropin was eluted off the column with 0.002 M $NH_4OAc$ (Stage $CMC_1$). Table 12. No activity was found in fractions corresponding to the behavior of LRH.

SEPARATION OF LRH FREE FROM FRH

Column Chromatography Separation

1. The sample in the phenol phase was next chromatographed on a 0.1% aqueous acetic acid-nBuOH-Pyr, 11-5-3, partition column (2 × 90 cm). Good activity for release of Luteotropin was found in tubes 4-26. Table 13. This corresponds to the behavior of LRH (Stage PC-$A_2$).

2. The sample in tubes 4-26 was submitted to ion exchange chromatography on a CMC column (1.5 × 30 cm). By using a continuous $NH_4OAc$ gradient 0.002 M pH 4.5 to 0.100 M pH 7, a fraction active in release of Luteotropin was eluted from the column with about 0.07 M $NH_4OAc$ Table 14. This behavior corresponds to that of LRH (Stage CMC).

CHART III: EXAMPLE III

Purification of Folliculotropin Releasing Hormones (FRH) on a Sephadex G-25 Partition Column Using nBuOH-HOAc-$H_2O$, 4-1-5, a System B Samples chromatographed twice on a Bio-Gel P-2 column have been further purified on a Sephadex G-25 partition column (2.5 × 90 cm), by use of the solvent system, nBuOH-HOAc-$H_2O$, (4-1-5). The column was prepared as described above. Several samples, weighing from 1.5 to 4.85 g have been fractionated. Between each separation the column was emptied and the gel extensively washed with lower phase. The column was then repacked and washed with upper phase before being used again.

Fractions of 10 ml were collected. The radioactive distribution in the fractions was determined and the contents of the tubes pooled according to this distribution FIG. IV. Assay data on some of these separations are in Table 15. The FRH activity was found in tubes 31–75 when a 2.5 × 90 cm column was used, and in tubes 21–45 when a 2.0 × 90 cm column was used. Five separations, making a total of 9,400 h.f.e. (19.0 g) yielded 4.2 g of FRH active fractions (Stage PC-B). Purification of Folliculotropin Releasing Hormone (FRH) on Sephadex LH-20.

Sephadex LH-20 was swollen in distilled water overnight and packed into a column (1.5 × 45 cm). The column was washed with 150 ml of distilled water-nbutanol (100-9 v/v). A 0.55 g (450 h.f.e.) sample, which had been purified twice on a Bio-Gel P-2 column, was fractionated on the column. Water-butanol (100-9 v/v) was used to elute the column, 10 ml fractions were collected. The best FRH activity was found in tubes 8–10. Table 16. (Stage PC-LH). When the column was equilibrated and eluted with water-butanol (100-6 v/v) the best FRH activity was recovered in tubes 6–8. Table 16.

ASSAY PROCEDURES FOR IN VITRO AND IN VIVO FOLLICULOTROPIN RELEASING HORMONE (FRH) AND LUTEOTROPIN RELEASING HORMONE (LRH) ASSAYS.

For the in vitro assays, pituitaries were obtained from female rats of the Sprague-Dawley strain which were 20 days old. Two pituitaries for each assay were incubated at 37° C in 1 ml of lactated Ringer's solution (Travenol Laboratories) in 10-ml Teflon beakers in a Dubnoff shaker. After a pre-incubation period of 1 hour ($PI_1$), the medium was removed for a control assay and fresh medium was added to the system. After a second hour of pre-incubation ($PI_2$), the medium was removed for assay and replaced. During the incubation (I), the medium was removed and assayed for release of pituitary hormones four times at one-hour periods, $I_3$, $I_4$, $I_5$, $I_6$. The samples to be assayed were added after the two-hour pre-incubation period; the total experimental time was 6 hours. LH was determined by the radioimmunoassay method of Niswender et al. (Niswender, et al., Proc. Soc. Exp. Biol. Med., 128, 807 (1968)), and FSH was determined according to Daane and Parlow (Daane and Parlow, Endocrinology, 88, 653 (1971)). The release of LH and FSH were evident by comparison of the pre-incubation and incubation values. The reagents for assay of FSH were generously distributed by Dr. A. Parlow of NIAMD, NIH; Dr. G. Niswender generously supplied the anti-ovine LH serum No. 15. Dr. L. E. Reichert, Jr. supplied the ovine LH preparation for labelling and the reference standard of LH from the rat. The values for these assays were calculated in terms of ng of the following reference standards: LH-LER-1240-2 (0.60 NIH-LH-S1 units/mg) and FSH 2.1 × NIH-FSH-S 1 units/mg.

The in vivo studies were performed in Sprague-Dawley adult female and male rats. Female rats were ovariectomized 2 or 3 months before the assays. All steroids were administered as a single injection, subcutaneously, 72 hours before injection of the decapeptide. Under ether anesthesia, blood was collected from the jugular vein and the decapeptide was injected into the same vein. Serum assays for LH and FSH were performed in duplicate by the double antibody radioimmunoassay of Niswender et al. and Daane and Parlow, respectively. The LH results are expressed in terms of ng/ml of LER 1240-2-0.6 NIH-LH-S-I units/mg and FSH in terms of a preparation with a potency of 2.1 × NIH-FSH-S-I units/mg.

SECTION B. The isolation of the Folliculotropin Releasing Hormone

CHART IV; EXAMPLE IV.

Extraction of Tissue For Standard Preparation (Stanprep) of Folliculotropin Releasing Hormone (FRH)

Fresh porcine hypothalamic tissues were placed in Nalgene bottles at the slaughter house. Each bottle contained 500 hypothalamic fragment equivalents (h.f.e.) in 400 ml of reagent grade methanol. The Nalgene bottles of hypothalami were shipped by air mail and were placed under refrigeration upon arrival.

The cold hypothalamic fragments in batches of 5,000 h.f.e. were collected by filtration through a large Buchner funnel without filter paper. The partially dried glands were then lyophilized. The decanted filtrate was saved for later use. The lyophilized tissue (about 500g/5,000 h.f.e.) is thoroughly homogenized in 4,000 ml of cold 15% by weight glacial acetic acid in methanol using a 1 gallon stainless steel Waring blender. The homogenate was allowed to stand for at least 1 hour in the cold room before filtration. The homogenate was filtered using a large Buchner funnel and Whatman No. 1 filter paper under reduced pressure. The filter cake was resuspended in 15% acetic acid in methanol and refiltered after at least 2 hours standing in the cold room. This procedure was repeated until a total of 5 filtrations had been accomplished. The resultant combined filtrates were evaporated to dryness under reduced pressure and added to the decanted filtrate from the tissue. The entire methanolic extract was evaporated to dryness.

The resultant dark brown, syrupy residue was dissolved in 350 to 400 ml of 2 M acetic acid (aqueous) and extracted three times with 400 ml of methylene chloride ($CH_2Cl_2$). The combined $CH_2Cl_2$ layer was backwashed with 150 ml of 2 M acetic acid and then extracted with 150 ml of $CH_2Cl_2$. The combined aqueous layers were then concentrated to dryness using a vacuum pump. The syrupy residue was taken up in about 300 ml of methanol and cooled to 0°C overnight. The resulting fine precipitate was removed by filtration and the filtrate evaporated to dryness to give 50 g of "Stanprep" having Folliculotropin Releasing Hormone (FRH) activity from 5000 h.f.e. The in vitro assay results are shown in Table 17.

Gel Filtration Chromatography of Folliculotropin Releasing Hormone on Bio-Gel P-2

Batches (50 g each) of "Stanprep" were dissolved in 100 ml of 1 M acetic acid and applied to a Bio-Gel P-2 column (5.0 × 135 cm) (100–200 mesh) ($V_0$ = 910ml) (Exclusion limit 1800 Daltons) that was previously equilibrated in the same solvent. The column was eluted using a 2–3 ft. pressure head of solvent and 14 ml fractions were collected. Appropriate fractions were pooled and an aliquot from each pooled fraction was submitted for biological assay. The assay results of the pooled fractions are shown in Table 18. As shown in Table 18. the Folliculotropin Releasing Activity (FRH) activity is located in Fractions No. 101–250. In general the gel filtration fractions are divided into four major groups:

|  |  | Wt. % | LRH and FRH Activity % |
|---|---|---|---|
| Group | A = No. 1–100 | Inactive 2.1 | 0 |
| " | B = No. 101–175 | Active 84.5 | 40–45 |
| " | C = No. 176–300 | Active 13.1 | 55–60 |
| " | D = No. 301–500 | Inactive .3 | 0 |

Group B fractions are then rechromatographed on the same Bio-Gel P-2 column described above. A similar weight and hormonal activity distribution is obtained.

|  |  | Wt. % | LRH and FRH Activity % |
|---|---|---|---|
| Group | BA = No. 1–100 | 2.3 | 0 |
| " | BB = 101–175 | 90.3 | 40–45 |
| " | BC = 176–300 | 7.1 | 55–60 |
| " | BD = 301–500 | 0.3 | 0 |

Group C fractions are combined from two identical columns, 10,000 h.f.e., and rechromatographed on Bio-Gel P-2. The in vitro assay data is shown in Table 19.

The activity and weight distribution is as shown:

|  |  | Wt. % | LRH and FRH Activity % |
|---|---|---|---|
| Group | CA = No. 1–100 | 0.7 | 0 |
| " | CB = 101–175 | 73.8 | 6 |
| " | CC = 176–275 | 25.2 | 94 |
| " | CD = 276–500 | 0.3 | 0 |

Group BC fractions are combined from two or three identical columns and rechromatographed to give similar results to those with combined Group C fractions. The in vitro assay data are shown in Table 20.

Folliculotropin Releasing Hormone (FRH) Partition Chromatography System A: n- Butanol-Pyridine-0.1% Acetic Acid (5:3:11).

A column (5.0 × 55 cm) was packed with Sephadex G-25 Fine that had been swollen overnight in the lower phase of the solvent system n-Butanol-Pyridine-0.1% acetic acid (5:3:11). The interstitial solvent that is excluded from the gel particles was replaced with the upper phase of solvent system A. A sample, 6.57g, was dissolved in 15 ml of the lower phase and applied to the top of the column. The column was eluted with the upper phase and 12 ml fractions were collected. After Fraction No. 300, the solvent was changed to lower phase of System A. The assay data is shown in Table 21. The activity and weight distribution is as shown below.

|  |  |  | Activity % | |
|---|---|---|---|---|
|  |  | Wt. % | LRH | FRH |
| Group A | 21–100 | 19.0 | 85 | 0 |
| Group B | 101–140 | 14.9 | 15 | <5 |
| Group C | 141–300 | 53.1 | 0 | 80 |
| Group D | 301–380 | 13.0 | 0 | <20 |

For smaller samples (3–4 g), a column (2.0 × 85 cm) packed in the same manner as above was used. The Folliculotropin Releasing Hormone (FRH) and Luteotropin Releasing Hormone (LRH) activity distribution is shown in Table 22 and the weight distribution is as shown for 10 ml fractions:

|  |  |  | Activity % | |
|---|---|---|---|---|
|  |  | Wt. % | LRH | FRH |
| Group A | 11–30 | 4.5 | 85 | 0 |
| Group B | 31–40 | 5.8 | 15 | <5 |
| Group C | 41–80 | 57.5 | 0 | 95 |
| Group D | 81–120 | 32.2 | 0 | <5 |

Folliculotropin Releasing Hormone (FRH): Partition Chromatography System B: n-Butanol-Acetic acid-Water (4:1:5)

A column (2.5 × 80 cm) was packed with Sephadex G-25 Fine swollen in the lower phase of the solvent system: n-Butanol-Acetic acid-Water (4:1:5). The interstitial solvent was then displaced with the upper phase. A sample of 3.67g from Partition Column A (FRH region) was dissolved in 5 ml of lower phase and applied to the top of the column. The column was eluted with the upper phase while collecting 10 ml fractions. The Folliculotropin Releasing Hormone (FRH) activity is shown in Table 23. The weight distribution is as shown below:

|  |  | Wt. % | FRH Activity % |
|---|---|---|---|
| Group I | 11–40 | 14.0 | 0 |
| Group II | 41–60 | 11.8 | 50 |
| Group III | 61–90 | 7.8 | 0 |
| Group IV | 91–110 | 66.4 | 50 |

Folliculotropin Releasing Hormone (FRH): Carboxymethylcellulose Chromatography

A column (1.5 × 80 cm) was packed with carboxymethyl cellulose that had been prepared by the method of Roy and Konigsberg (Roy and Konigsberg, Methods in Enzymology, 25, 221 (1972)) and then equilibrated with 2 mM pH 4.5 $NH_4OAc$. A sample, 2.03 g, of FRH from Partition Column System A was dissolved in 10 ml of starting buffer and applied to the column. A linear gradient to 100 m M, pH 7 $NH_4OAc$ was started at fraction No. 11 and fractions of 10 ml were collected. A small amount of LRH activity present in the starting material appears in Fraction No. 61–65 (70 m M). The FRH activity (1.62 g) was unretained and was eluted in Fractions No. 6–10. The assay results are shown in Table 24.

CHART V; EXAMPLE V.

Folliculotropin Releasing Hormone (FRH) Chromatography on Bio-Rad AG-11A8 Ion Retardation Resin A sample of 2.25 g of FRH from Partition Column System A was dissolved in 15 ml of water and applied to a column (1.5 × 80 cm) of Bio-Rad AG-11A8 (50-100 mesh) resin. The column was eluted with water while collecting 10 ml fractions and finally eluted with 1 M acetic acid. The FRH assay results, in vitro, are shown in Table 25. The weight and activity distribution is as shown:

|  |  |  | Activity % | |
|---|---|---|---|---|
|  |  | Wt. % | LRH | FRH |
| Group I | 1–20 | 74.2 | 100 | 25 |
| Group II | 21–40 | 8.5 | 0 | 0 |
| Group III | 41–70 | 8.6 | 0 | 0 |
| Group IV | 71–165 | 1.1 | 0 | 15 |
| Group V | 1 M HOAc | 7.6 | 0 | 60 |

Diethylaminoethylcellulose Chromatography

A column (1.5 × 25 cm) was packed with DEAE cellulose prepared by the method of Roy and Konigsberg. The column was equilibrated with 2 mM, pH 9, $NH_4OAc$ and a sample of 0.69 g of FRH from Partition Column A and desalting on Bio-Rad AG-11A8. The column was eluted with a continuous linear gradient buffer to pH 7, 100 mM $NH_4OAc$. The column was then washed with 2 M HOAc. The activity and weight distribution is shown below. In vitro assay results of pooled fractions (5 ml) are in Table 26.

Folliculotropin Releasing Hormone (FRH): Cellulose Thin Layer Chromatography

A sample of FRH from Partition Column System A-Ion Retardation resin Group I was divided and chromatographed on two identical Cellulose TLC plates. One plate was developed in Chloroform-Methanol-Aqueous $NH_4OH$ (60:45:20) and the second plate was developed in Chloroform-Methanol-32% Aqueous Acetic acid (60:45:20). The FRH activity is shown in Table 27.

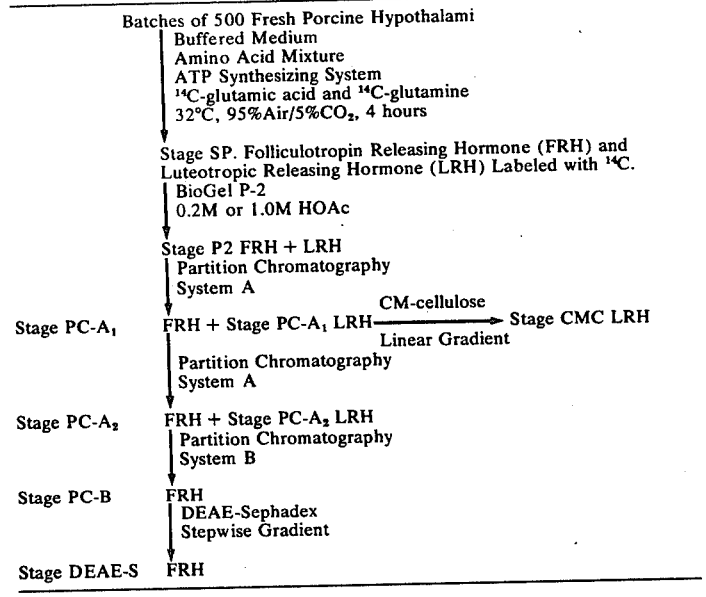

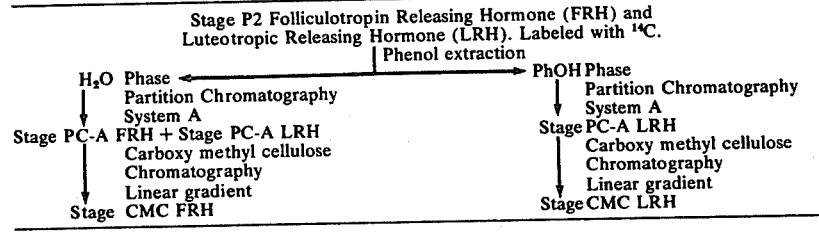

|  |  | Wt. % | Activity % |
|---|---|---|---|
| Group I | 6–10 | 72.4 | <5 |
| Group II | 11–70 | 20.2 | 0 |
| Group III | 71–110 | 2.8 | 0 |
| Group IV | 2 M HOAc | 4.3 | <95 |

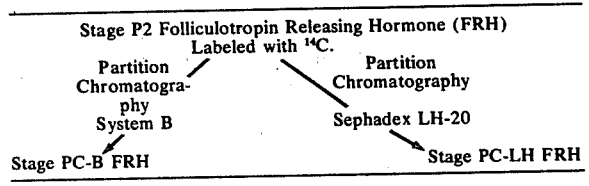

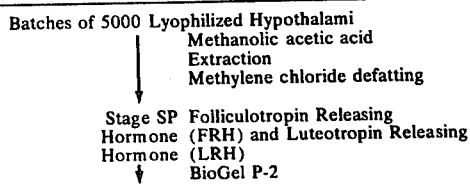

CHART IV EXAMPLE IV -continued

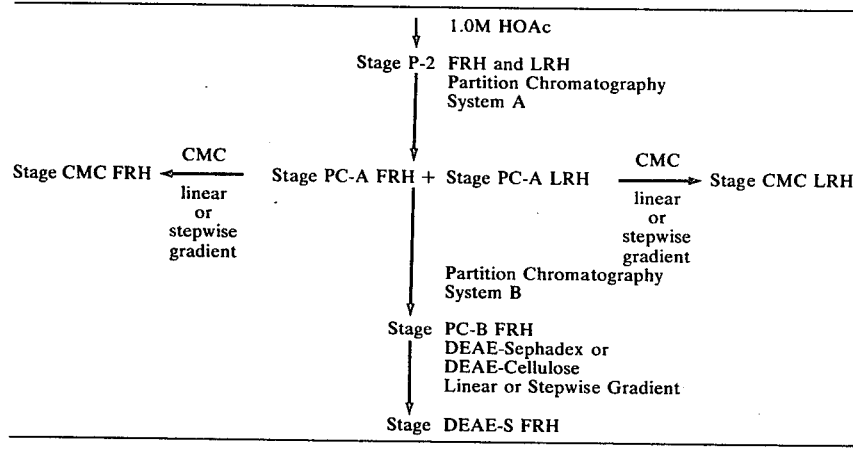

```
                                      │ 1.0M HOAc
                                      ▼
                          Stage P-2  FRH and LRH
                                     Partition Chromatography
                                     System A
                                      │
         CMC                          ▼                CMC
Stage CMC FRH ◄─────── Stage PC-A FRH + Stage PC-A LRH ────► Stage CMC LRH
         linear                                       linear
         or                                           or
         stepwise                                     stepwise
         gradient                                     gradient
                                     Partition Chromatography
                                     System B
                                      │
                                      ▼
                          Stage PC-B FRH
                                     DEAE-Sephadex or
                                     DEAE-Cellulose
                                     Linear or Stepwise Gradient
                                      │
                                      ▼
                          Stage DEAE-S FRH
```

CHART V EXAMPLE V

```
Stage PC-A FRH
    │  Bio Rad AG-11A8
    │  Ion Retardation
    │  Resin, H₂O then HOAc
    ▼
Stage AG FRH
    ╱      ╲
   cellulose        DEAE-Cellulose
     TLC            Linear Gradient
    ╱                       ╲
Stage TLC FRH         Stage DEAE-C FRH
```

Table 1

In Vitro Assay of Folliculotropin Releasing Hormone (FRH) and Luteotropin Releasing Hormone (LRH) in Stanpreps Stage SP)

| IBR No. | Description | h.f.e. | Preincubation | | | ng FSH/ml Incubation | | |
|---|---|---|---|---|---|---|---|---|
| | | | $P_1$ | $P_2$ | $I_3$ | $I_4$ | $I_5$ | $I_6$ |
| 2933 | SP 101 | 0.6, 3.0 | 1000 | <1000 | 12,500 | 52,000 | 60,000 | 52,000 |
| 3163 | SP 102 | 0.5, 7.5 | 1250 | <1000 | 3,250 | 38,750 | >128,000 | 46,250 |
| 3388 | SP 105 | 0.5, 2.5 | — | 1800 | — | 17,750 | 51,750 | — |
| | | | | | | ng LH/ml | | |
| 2933 | SP 101 | 0.6, 3.0 | 20 | 20 | 378 | >714 | >714 | >714 |
| 3163 | SP 102 | 0.5, 7.5 | 20 | 38 | 165 | >714 | >714 | >714 |

Table 2

In Vitro Assay of Folliculotropin Releasing Hormone (FRH) and Luteotropin Releasing Hormone (LRH) in Samples From First Bio-Gel P-2 Separation (Stage P-2)

| IBR No. | Description | h.f.e. | Preincubation | | | ng FSH/ml Incubation | | |
|---|---|---|---|---|---|---|---|---|
| | | | $P_1$ | $P_2$ | $I_3$ | $I_4$ | $I_5$ | $I_6$ |
| 2910 | SP 101 | 0.2, 3 | <1000 | <1000 | 9000 | 10,750 | 42,000 | 68,000 |
| 2915 | SP 101 | 0.2, 3 | 1000 | <1000 | 26,000 | 37,500 | 126,000 | 51,000 |
| 3165 | SP 102 | 0.2, 2 | 2000 | 2750 | 17,150 | 13,500 | 52,500 | >128,000 |
| 3167 | SP 102 | 0.2, 2 | 2300 | 2650 | 28,000 | 34,000 | 67,500 | 43,250 |
| 3168 | SP 102 | 0.2, 2 | 53000 | 4300 | 10,150 | 8,900 | >128,000 | 64,750 |
| 3276 | SP 104 | 0.2, 1 | 3000 | 3500 | 20,000 | — | 76,750 | 68,500 |
| 3277 | SP 104 | 0.2, 1 | 5000 | 5000 | 110,000 | — | 68,500 | 54,000 |
| 3278 | SP 104 | 0.2, 1 | 5000 | 4500 | 64,000 | — | 59,500 | 39,250 |
| 3392 | SP 105 | 0.1, 0.5 | — | 1650 | — | 12,650 | 12,250 | — |
| 3393 | SP 105 | 0.1, 0.5 | — | 1900 | — | 13,500 | 16,500 | — |
| 3394 | SP 105 | 0.1, 0.5 | — | 5150 | — | 5,050 | 7,600 | — |
| | | | | | | ng LH/ml | | |
| 2910 | SP 101 | 0.2, 3 | 14 | 13 | 151 | 168 | >714 | >714 |
| 2915 | SP 101 | 0.2, 3 | 20 | 20 | 131 | 528 | >714 | >714 |
| 3165 | SP 102 | 0.2, 2 | 50 | 60 | 155 | 258 | >714 | >714 |
| 3167 | SP 102 | 0.2, 2 | 63 | 50 | 375 | 662 | >714 | >714 |
| 3168 | SP 102 | 0.2, 2 | 225 | 88 | 80 | 115 | >714 | >714 |
| 3276 | SP 104 | 0.2, 1 | 25 | 29 | 215 | 490 | >714 | >714 |
| 3277 | SP 104 | 0.2, 1 | 126 | 208 | 405 | 683 | >714 | >714 |
| 3278 | SP 104 | 0.2, 1 | 294 | 148 | 692 | 714 | >714 | >714 |

Table 3

In Vitro Assay of Folliculotropin Releasing Hormone
(FRH) in Pooled Samples From Second Bio-Gel P-2
Separation (Stage P-2)

| IBR No. | Description | h.f.e. | Preincubation | | | Incubation | | |
|---|---|---|---|---|---|---|---|---|
| | | | $P_1$ | $P_2$ | $I_3$ | $I_4$ | $I_5$ | $I_6$ |
| 3432 | IBR 101–105 | 0.2, 1 | — | 2000 | — | 8100 | 25,700 | — |
| 3433 | " | " | — | 1750 | — | 19100 | 34,650 | — |
| 3434 | " | " | — | 1250 | — | 11400 | 29,950 | — |
| 3435 | " | " | — | 2250 | — | 12550 | 15,600 | — |
| 3436 | " | " | — | 3500 | — | 8250 | 19.950 | — |
| 3437 | " | " | — | 2500 | — | 9800 | 14,600 | — |
| 3438 | " | " | — | 3100 | — | 9100 | 43,250 | — | ng FSH/ml

Table 4

In Vivo Assay of Luteotropin Releasing Hormone
(LRH) in Samples from Stage PC-$A_1$

| IBR | Description | Tubes | h.f.e. | Before | After |
|---|---|---|---|---|---|
| 2748 | May 5 | 11–35 | 3 | 7.2 | 224 |
| | | | | 12 | 127 |
| 2749 | May 5 | 36–55 | 3 | 12 | 25.2 |
| | | | | 9.2 | 12 |
| 7750 | May 5 | 56–75 | 3 | 15.6 | 12.6 |
| 7751 | May 5 | 76–100 | 3 | 7.2 | 39 |
| | | | | 7.6 | 12 |
| | | | | 8 | 96 |

Table 5

In Vitro Assay of Folliculotropin Releasing Hormones
(FRH) and Luteotropin Releasing Hormone (LRH) in
Samples from Stage PC-$A_1$ ng FSH/ml

| IBR No. | Description | Tubes | h.f.e. | Preincubation | | | Incubation | | |
|---|---|---|---|---|---|---|---|---|---|
| | | | | $P_1$ | $P_2$ | $I_3$ | $I_4$ | $I_5$ | $I_6$ |
| 2976 | May 5 | 36–55 | 1,5 | 2400 | 1250 | 2,250 | 17,100 | 56,500 | 51,150 |
| 2977 | May 5 | 56–75 | 1,5 | 2000 | 1900 | 121,000 | 112,500 | 38,000 | 30,750 |
| 2978 | May 5 | 76–100 | 1,5 | 1000 | 1000 | 55,500 | 46,750 | 40,500 | 16,600 | ng LH/ml

| 2976 | May 5 | 36–55 | 1,5 | 78 | 58 | 115 | 340 | > 714 | > 714 |
| 2977 | May 5 | 56–75 | 1,5 | 138 | 50 | > 714 | > 714 | > 714 | > 714 |
| 2978 | May 5 | 26–100 | 1,5 | 30 | 40 | > 714 | > 714 | > 714 | > 714 |

Table 6

In Vitro Assay of Folliculotropin Releasing Hormone (FRH) and
Luteotropin Releasing Hormone (LRH) in Samples from Stage PC-$A_2$ ng FSH/ml

| IBR No. | Description | Tubes | h.f.e. | Preincubation | | | Incubation | | |
|---|---|---|---|---|---|---|---|---|---|
| | | | | $P_1$ | $P_2$ | $I_3$ | $I_4$ | $I_5$ | $I_6$ |
| 3213 | May 5 | 11–25 | 1,5 | 5000 | 4000 | 8,000 | — | 17,500 | 18,000 |
| 3214 | May 5 | 26–45 | 1,5 | 3000 | 5000 | 4,000 | — | 4,500 | 5,500 |
| 3215 | May 5 | 46–65 | 1,5 | 3500 | 5000 | 52,000 | — | 40,000 | 28,250 |
| 3216 | May 5 | 66–85 | 1,5 | 3300 | 4500 | 33,000 | — | 67,000 | 47,500 |
| 3217 | May 5 | 86–112 | 1,5 | 4000 | 4000 | 5,000 | — | 25,000 | 55,500 | ng LH/ml

| 3213 | May 5 | 11–25 | 1,5 | 94 | 79 | 179 | 168 | 460 | 555 |
| 3214 | May 5 | 26–45 | 1,5 | 25 | 10 | 18 | 14 | 29 | 41 |
| 3215 | May 5 | 46–65 | 1,5 | 201 | 142 | 622 | 717 | > 714 | >714 |
| 3216 | May 5 | 66–85 | 1,5 | 59 | 69 | 358 | 535 | > 714 | >714 |
| 3217 | May 5 | 86–112 | 1,5 | 39 | 48 | 30 | 123 | 243 | 617 |

Table 7

In Vitro Assay of Folliculotropin Releasing Hormone in Samples from Stage PC-B

| IBR No. | Description | Tubes | h.f.e. | ng FSH/ml Preincubation $P_1$ | $P_2$ | Incubation $I_3$ | $I_4$ | $I_5$ | $I_6$ |
|---|---|---|---|---|---|---|---|---|---|
| 3421 | May 5 | 5–25 | 2,10 | — | 1500 | — | 4,900 | 8,650 | — |
| 3422 | May 5 | 26–40 | 2,10 | — | 2000 | — | 33,250 | 43,500 | — |
| 3423 | May 5 | 41–50 | 2,10 | — | 2000 | — | 3,650 | 5,000 | — |
| 3425 | May 5 | 51–70 | 2,10 | — | 1250 | — | 2,500 | 4,750 | — |

Table 8

In Vitro Assay of Folliculotropin Releasing Hormone (FRH) and Luteotropin Releasing Hormone (LRH) in Samples from Stage DEAE-S.

| IBR No. | Description | Fraction | ng FSH/ml Preincubation $P_1$ | $P_2$ | Incubation $I_3$ | $I_4$ | $I_5$ | $I_6$ |
|---|---|---|---|---|---|---|---|---|
| 3652 | May 5 | 0.04 M | — | 2400 | — | 6500 | 3,550 | — |
| 3653 | May 5 | 0.06 M | — | 1900 | — | 4700 | 3,600 | — |
| 3654 | May 5 | 0.08 M | — | 2600 | — | 6400 | 4,300 | — |
| 3656 | May 5 | 0.5 M | — | 2600 | — | — | 90,750 | — |

| | | | ng LH/ml | | | | | |
|---|---|---|---|---|---|---|---|---|
| 3656 | May 5 | 0.5 M | — | 130 | — | 445 | > 714 | — |

Table 9

In Vitro Assay of Folliculotropin Releasing Hormone (FRH) and Luteotropin Releasing Hormone (LRH) in Samples from Stage CMC.

| IBR No. | Description | Fraction | ng FSH/ml Preincubation $P_1$ | $P_2$ | Incubation $I_3$ | $I_4$ | $I_5$ | $I_6$ |
|---|---|---|---|---|---|---|---|---|
| 2981 | May 5 | 0.002 M | 2250 | 2600 | 9,600 | 15,500 | 19,250 | 22,750 |
| 2982 | May 5 | 0.01 M | 1000 | 1350 | 7,950 | 5,250 | 11,000 | 14,150 |
| 2983 | May 5 | 0.04 M | 1900 | 2500 | 7,700 | 3,750 | 12,000 | 13,000 |
| 2984 | May 5 | 0.07 M | 3050 | 1850 | 12,250 | 19,500 | 30,750 | 34,250 |
| 2985 | May 5 | 0.100 M | 1000 | 2000 | 2,850 | 4,500 | 6,000 | 6,500 |

| | | | ng LH/ml | | | | | |
|---|---|---|---|---|---|---|---|---|
| 2981 | May 5 | 0.002 M | 20 | 40 | 165 | 296 | > 714 | 560 |
| 2982 | May 5 | 0.01 M | 30 | 39 | 228 | 150 | 348 | 515 |
| 2983 | May 5 | 0.04 M | 30 | 44 | 157 | 85 | 398 | 365 |
| 2984 | May 5 | 0.07 M | 121 | 50 | 283 | > 714 | > 714 | >714 |
| 2985 | May 5 | 0.100 M | 32 | 41 | 80 | 125 | 208 | 113 |

Table 10

In Vivo Assay of Folliculotropin Releasing Hormone (FRH) and Luteotropin Releasing Hormone (LRH) in Samples from Phenol Extraction of Stage P-2 Preparations.

| IBR No. | Description | Phase | h.f.e. | ng FSH/ml Before | After |
|---|---|---|---|---|---|
| 2338 | Jan. 20 | PhOH | 0.5 | 3330 | 2800 |
| | | | | 3210 | 2890 |
| 2339 | Jan. 20 | H$_2$O | 5 | 4260 | 4990 |
| | | | | 3400 | 4680 |

| | | | | ng LH/ml | |
|---|---|---|---|---|---|
| 2338 | Jan. 20 | PhOH | 0.5 | 6 | 25 |
| | | | | 4 | 27 |
| 2338 | Jan. 20 | H$_2$O | 5 | 16 | 74 |
| | | | | 12 | 79 |

Table 11

In Vivo Assay of Folliculotropin Releasing Hormone (FRH) and Luteotropin Releasing Hormone (LRH) in Samples from Stage PC-A

| IBR No. | Description | Fraction | ng FSH/ml Before | After |
|---|---|---|---|---|
| 2602 | Jan. 20 | 1–27 | 3800 | 3300 |
| 2604 | Jan. 20 | 56–80 | 2850 | 2950 |
| | | | 2850 | 2800 |
| 2605 | Jan. 20 | 81–102 | 2350 | 3300 |
| | | | 1800 | 2000 |

| | | | ng LH/ml | |
|---|---|---|---|---|
| 2602 | Jan. 20 | 1–27 | 14 | 62 |
| | | | 14 | 43 |
| 2604 | Jan. 20 | 56–80 | 14 | 33 |
| | | | 8 | 50 |
| 2605 | Jan. 20 | 81–102 | < 4 | 242 |
| | | | 6 | 23 |

Table 12

In Vitro Assay of Folliculotropin Releasing Hormone (FRH) and Luteotropin Releasing Hormone (LRH) in Samples from Stage $CMC_1$

| IBR No. | Description | Fraction | ng FSH/ml Preincubation $P_1$ | $P_2$ | Incubation $I_3$ | $I_4$ | $I_5$ | $I_6$ |
|---|---|---|---|---|---|---|---|---|
| 2704 | Jan. 20 | 0.002 M | < 1000 | 2100 | 10250 | 1900 | 55,500 | 59,500 |
| 2705 | Jan. 20 | 0.01 M | 2400 | 3950 | 12000 | 8750 | 28,500 | 28,500 |
| 2706 | Jan. 20 | 0.04 M | 1050 | 2000 | 2500 | 2350 | 4,000 | 3,750 |
| 2707 | Jan. 20 | 0.07 M | 1000 | 1800 | 2300 | 2150 | 3,250 | 3,750 |
| 2708 | Jan. 20 | 0.10 M | 1250 | 2050 | 2200 | 3300 | 3,500 | 3,250 |

| IBR No. | Description | Fraction | ng LH/ml $P_1$ | $P_2$ | $I_3$ | $I_4$ | $I_5$ | $I_6$ |
|---|---|---|---|---|---|---|---|---|
| 2704 | Jan. 20 | 0.002 M | < 10 | 10 | 260 | 525 | > 714 | > 714 |
| 2705 | Jan. 20 | 0.01 M | 65 | 20 | 340 | 415 | > 714 | 582 |
| 2706 | Jan. 20 | 0.04 M | 20 | 20 | 40 | 53 | 68 | 38 |
| 2707 | Jan. 20 | 0.07 M | 26 | 20 | 50 | 35 | 60 | 40 |
| 2708 | Jan. 20 | 0.10 M | 10 | 10 | 18 | 50 | 38 | 70 |

Table 13

In Vivo Assay of Folliculotropin Releasing Hormone (FRH) and Luteotropin Releasing Hormone (LRH) in Samples from Stage $PC-A_2$

| IBR | Description | Fraction | ng FSH/ml Before | After |
|---|---|---|---|---|
| 2340 | Jan. 20 | 4–26 | 3200 | 3830 |
|  |  |  | 5300 | 5160 |

| IBR | Description | Fraction | ng LH/ml Before | After |
|---|---|---|---|---|
| 2340 | Jan. 20 | 4–26 | 4 | >285 |
|  |  |  | 10 | 263 |
| 2341 | Jan. 20 | 27–40 | 14 | 16 |
|  |  |  | <4 | <4 |
| 2342 | Jan. 20 | 41–55 | 12 | 15 |
|  |  |  | 10 | 11 |
| 2559 | Jan. 20 | 56–80 | 6 | 8 |
|  |  |  | <4 | <4 |
| 2560 | Jan. 20 | 81–100 | 4 | 4 |
|  |  |  | <4 | 15 |

Table 14

In Vivo Assay of Luteotropin Releasing Hormone (LRH) in Samples from Stage CMC

| IBR | Description | Fraction | ng LH/ml Before | After |
|---|---|---|---|---|
| 2564 | Jan. 20 | 0.002 M | <4 | <4 |
|  |  |  | 6 | 6 |
| 2565 | Jan. 20 | 0.01 M | <4 | 24.5 |
|  |  |  | 6 | 12 |
| 2566 | Jan. 20 | 0.02 M | 10 | 14 |
|  |  |  | 12 | 14 |
| 2567 | Jan. 20 | 0.04 M | 6 | 6 |
|  |  |  | 8 | 6.4 |
| 2568 | Jan. 20 | 0.05 M | 7 | 8 |
|  |  |  | 4 | 4 |
| 2569 | Jan. 20 | 0.07 M | 4 | 54.2 |
|  |  |  | 4 | 72.0 |
| 2570 | Jan. 20 | 0.10 M | 4 | 4 |
|  |  |  | 4 | 4 |

Table 15

In Vitro Assay of Folliculotropin Releasing Hormone (FRH) in Samples from Stage PC-B

| IBR No. | Description | Fraction | ng FSH/ml Preincubation $P_1$ | $P_2$ | Incubation $I_3$ | $I_4$ | $I_5$ | $I_6$ |
|---|---|---|---|---|---|---|---|---|
| 3753 | SP101–105 | 24–40 | — | 3250 | — | — | 50,500 | — |
| 3794 | SP101–105 | 21–45 | — | 2600 | — | 46,000 | 43,000 | — |
| 3797 | SP101–105 | 36–75 | — | 2600 | — | 51,000 | 41,250 | — |

Table 16

In Vitro Assay of Folliculotropin Releasing Hormone (FRH) in Samples from Stage PC-LH

| IBR No. | Description | Fraction | ng FSH/ml Preincubation $P_1$ | $P_2$ | Incubation $I_3$ | $I_4$ | $I_5$ | $I_6$ |
|---|---|---|---|---|---|---|---|---|
| 3747 | SP101–105 9% BuOH | 8–10 | — | 3350 | — | — | 54500 | — |
| 3733 | SP101–105 6% BuOH | 6–8 | — | 3150 | — | — | 46700 | — |

Table 17

In Vitro Assay of Folliculotropin Releasing Hormone (FRH) in Stanprep (Stage SP)

| IBR No. | Description | Wt. of dose, mg | Preincubation | | Incubation ng FSH/ml | | | |
|---|---|---|---|---|---|---|---|---|
| | | | $P_1$ | $P_2$ | $I_3$ | $I_4$ | $I_5$ | $I_6$ |
| 3093 | DH-133 | 3.7,18.7 | 1450 | 3600 | 31,500 | 51,500 | 52,500 | 39,000 |
| 3023 | FK-I | 5.6,29.1 | 1000 | 1500 | 13,750 | 18,900 | 46,000 | >128,000 |
| 3173 | FK-II | 3.9,19.4 | 2850 | 3600 | 20,600 | 51,500 | 54,750 | 26,250 |
| 3777 | FK-III | 27.5 | — | 2300 | — | — | 35,500 | — |

Table 18

In Vitro Assay of Folliculotropin Releasing Hormone (FRH) from Pooled Fractions After Bio-Gel P-2 Chromatography of 5000 h.f.e. (Stage P-2)

| IBR No. | Description | Preincubation | | Incubation ng FSH/ml | | | |
|---|---|---|---|---|---|---|---|
| | | $P_1$ | $P_2$ | $I_3$ | $I_4$ | $I_5$ | $I_6$ |
| 3025 | FK-I-101–125 | 2400 | 2300 | 4650 | 3750 | 17,250 | 35,750 |
| 3026 | FK-I-126–150 | 2400 | 3600 | 38,500 | 104,500 | >128,000 | 40,250 |
| 3027 | FK-I-151–175 | 4000 | 3550 | 58,250 | >128,000 | >128,000 | 53,500 |
| 3028 | FK-I-176–200 | 4050 | 4250 | 14,500 | >128,000 | >128,000 | 49,000 |
| 3029 | FM-I-201–225 | 2800 | 2500 | 36,750 | 92,500 | >128,000 | >128,000 |
| 3030 | FK-I-226–250 | 3500 | 3350 | 10,000 | 18,150 | 38,650 | 34,000 |
| 3095 | DH-125-101–125 | 7300 | 8500 | 24,500 | 16,600 | 16,150 | 19,750 |
| 3096 | DH-125-126–150 | 9350 | 7000 | 33,500 | 35,000 | 32,500 | 41,000 |
| 3097 | DH-125-151–175 | <1000 | 1600 | 40,500 | 51,750 | 38,500 | 24,000 |
| 3098 | DH-125-176–200 | 2050 | 4000 | 49,500 | 39,000 | 22,100 | 21,250 |
| 3099 | DH-125-201–250 | 6000 | 8000 | 25,250 | 22,750 | 49,000 | 39,000 |
| 2995 | DH-128-180–359 | 3600 | 3250 | 33,750 | 58,000 | >128,000 | 100,000 |

Table 19

In Vitro Assay of Folliculotropin Releasing Hormone (FRH) from Pooled Fractions After Rechromatography on Bio-Gel P-2 of 10,000 h.f.e. (No. 180–360) (Stage P-2)

| IBR No. | Description | Preincubation | | Incubation ng FSH/ml | | | |
|---|---|---|---|---|---|---|---|
| | | $P_1$ | $P_2$ | $I_3$ | $I_4$ | $I_5$ | $I_6$ |
| 2997 | DH-128-101–125 | 1950 | 3500 | 14,500 | 22,750 | 39,500 | 30,250 |
| 2998 | DH-128-126–150 | 2150 | 4000 | 10,350 | 10,750 | 10,000 | 13,000 |
| 2999 | DH-128-151–175 | 2050 | 4000 | 5750 | 5750 | 19,750 | 38,750 |
| 3000 | DH-128-176–200 | 1100 | 3000 | 61,000 | 76,500 | 76,500 | 32,250 |
| 3001 | DH-128-201–225 | 2850 | 3250 | 40,500 | 73,500 | 83,000 | 40,000 |
| 3003 | DH-128-226–250 | 1100 | 1000 | 5,600 | 7,100 | 43,500 | 43,750 |
| 3456 | DH-129-2-106–175 | — | 2750 | — | 22,000 | 47,750 | — |
| 3457 | DH-129-2-176–275 | — | 2250 | — | 23,000 | 27,650 | — |
| 3515 | DH-129-3-101–175 | — | <1000 | — | 17,256 | 36,500 | — |
| 3516 | DH-129-3-176–300 | — | <1000 | — | 37,250 | 27,250 | — |

Table 20

In Vitro Assay of Folliculotropin Releasing Hormone (FRH) Fractions After Rechromatography of Group B Fractions From First P-2 (Stage P-2)

| IBR No. | Description | Preincubation | | Incubation | | | |
|---|---|---|---|---|---|---|---|
| | | $P_1$ | $P_2$ | $I_3$ | $I_4$ | $I_5$ | $I_6$ |
| 3518 | FK-II-101–175 | — | <1000 | — | 45,500 | 43,000 | — |
| 3519 | FK-II-176–300 | — | <1000 | — | 56,250 | 50,500 | — |
| 3602 | FK-I-101–175 | — | 4150 | — | 65,250 | 28,000 | — |
| 3603 | FK-I-176–300 | — | 2350 | — | 66,750 | 30,150 | — |
| 3605 | DH-115-101–175 | — | 3550 | — | 87,000 | 71,750 | — |
| 3606 | DH-115-176–319 | — | 4900 | — | 51,900 | 81,500 | — |

Table 21

In Vitro Assay of Folliculotropin Releasing Hormone (FRH) of Fractions from Partition Column: System A. (5.0×55 cm column) (Stage PC-A)

| IBR No. | Description | Wt. of dose, mg | Preincubation | | Incubation | | | |
|---|---|---|---|---|---|---|---|---|
| | | | $P_1$ | $P_2$ | $I_3$ | $I_4$ | $I_5$ | $I_6$ |
| 3554 | DH-129-21–40 | 0.1,0.5 | — | 1300 | — | 6,500 | 16,950 | — |
| 3528 | DH-129-41–60 | 0.4,1.8 | — | 1350 | — | 14,350 | 28,250 | — |
| 3529 | DH-129-81–100 | 1.6,8.3 | — | 1650 | — | 2,300 | 21,500 | — |
| 3530 | DH-129-101–120 | 1.1,5.8 | — | <1000 | — | <1,000 | 5,500 | — |
| 3531 | DH-129-121–140 | 1.1,5.4 | — | 1250 | — | 6,300 | 25,300 | — |
| 3532 | DH-129-141–160 | 0.7,3.5 | — | 2600 | — | 15,800 | 62,500 | — |
| 3533 | DH-129-161–180 | 1.6,8.3 | — | 1000 | — | 46,900 | 45,750 | — |
| 3534 | DH-129-181–200 | 2.1,10.6 | — | <1000 | — | 42,600 | 36,900 | — |
| 3535 | DH-129-201–220 | 1.4,6.9 | — | <1000 | — | 41,500 | 37,250 | — |
| 3536 | DH-129-221–240 | 0.8,4.1 | — | 1850 | — | 27,300 | 56,750 | — |
| 3537 | DH-129-261–280 | 0.5,2.3 | — | 1350 | — | 14,750 | 58,000 | — |
| 3538 | DH-129-301–320 | 0.3,1.5 | — | <1000 | — | 1,500 | 18,000 | — |
| 3635 | DH-129-321–340 | 1.4,5.8 | — | 2450 | — | 18,750 | 69,500 | — |
| 3636 | DH-129-341–360 | 0.7,3.4 | — | 2200 | — | 9,750 | 37,500 | — |
| 3637 | DH-129-361–380 | 0.1,0.6 | — | 1300 | — | 4,250 | 3,000 | — |

Table 22

In Vitro Assay of Folliculotropin Releasing Hormone (FRH) in Fractions from Partition Column. System A. (2.0×85 column) (Stage PC-A)

| IBR No. | Description | Wt. of dose, mg | Preincubation | | Incubation | | | |
|---|---|---|---|---|---|---|---|---|
| | | | $P_1$ | $P_2$ | $I_3$ | $I_4$ | $I_5$ | $I_6$ |
| 3076 | DH-128-51–70 | | <1000 | 1550 | 39,500 | 34,000 | 53,500 | 41,250 |
| 3079 | DH-128-101–120 | | 1000 | <1000 | 1,000 | 1,100 | 2,600 | 3,650 |
| 3116 | DH-128-141–160 | | 4100 | 4500 | 4,000 | 4,000 | 3,500 | 2,650 |
| 3117 | BC-57-11–20 | | 3700 | 5250 | 16,750 | 12,500 | 19,750 | 4,750 |
| 3118 | BC-57-21–30 | | 5500 | 5750 | 22,500 | 4,750 | 14,750 | 16,250 |
| 3119 | BC-57-31–40 | | 2500 | 4750 | 5,100 | 6,250 | 9,150 | 8,850 |
| 3120 | BC-57-41–50 | | 3350 | 3150 | 27,000 | 37,500 | 49,500 | 46,500 |
| 3121 | BC-57 51–60 | | 3500 | 3500 | 33,800 | 51,000 | 42,000 | 30,000 |
| 3122 | BC-57 61–70 | | 1950 | 1550 | 39,500 | 63,100 | 49,500 | 40,000 |
| 3147 | BC-57 71–80 | | 2100 | 3050 | 4,000 | 6,600 | 25,250 | 36,250 |
| 3148 | BC-57 81–90 | | 3100 | 3650 | 1,750 | 1,350 | 2,500 | 3,250 |
| 3149 | BC-57 90–100 | | 5740 | 4950 | 3,000 | 3,300 | 2,200 | 2,750 |
| 3152 | BC-57-2- | | | | | | | |

Table 22-continued

In Vitro Assay of Folliculotropin Releasing Hormone (FRH)
in Fractions from Partition Column. System A. (2.0×85 column)
(Stage PC-A)

| IBR No. | Description | Wt. of dose, mg | Preincubation | | Incubation (ng FSH/ml) | | | |
|---|---|---|---|---|---|---|---|---|
| | | | $P_1$ | $P_2$ | $I_3$ | $I_4$ | $I_5$ | $I_6$ |
| 3153 | BC-57-2-21–30 | | 1000 | 1400 | 2,350 | 3,100 | 2,500 | 2,750 |
| 3154 | BC-57-2-31–40 | | 1200 | 1600 | 2,000 | 1,750 | 3,000 | 1,900 |
| 3155 | BC-57-2-41–45 | | 4450 | 5250 | 4,500 | 5,000 | 6,750 | 3,000 |
| 3760 | BC-57-2-46–55 | | 1050 | 1300 | 39,900 | 48,500 | 45,000 | 30,000 |
| 3761 | BC-63-21–30 | 0.1,0.5 | — | 3050 | — | — | 3,300 | — |
| 3762 | BC-63-31–40 | 0.2,1.1 | — | 4550 | — | — | 4,400 | — |
| 3814 | BC-63-41–50 | 0.5,2.4 | — | 3400 | — | — | 9,250 | — |
| 3815 | BC-63-51–60 | 0.7,3.7 | — | 3000 | — | 24,000 | 69,500 | — |
| 3763 | BC-63-61–70 | 0.4,2.1 | — | 3000 | — | 2,500 | 4,000 | — |
| 3764 | BC-63-71–80 | 0.3,1.5 | — | 2650 | — | — | 2,250 | — |
| | BC-63-81–113 | 0.8,4.0 | — | 4050 | — | — | 5,500 | — |

Table 23

In Vitro Assay of Folliculotropin Releasing Hormone
(FRH in Fraction from Partition Column System B. (2.5×80 cm)
(Stage PC-B)

| IBR No. | Description | Wt. of dose,mg | Preincubation | | | | Incubation (ng FSH/ml) | |
|---|---|---|---|---|---|---|---|---|
| | | | $P_1$ | $P_2$ | $I_3$ | $I_4$ | $I_5$ | $I_6$ |
| 3765 | DH-129-A-11–25 | | — | 3650 | — | — | 2950 | — |
| 3766 | " 26–40 | | — | 4350 | — | — | 3600 | — |
| 3767 | " 41–50 | 2.3 | — | 4800 | — | — | 22,000 | — |
| 3768 | " 51–60 | 2.0 | — | 2950 | — | — | 46,150 | — |
| 3769 | " 61–70 | | — | 3800 | — | — | 1500 | — |
| 3770 | " 91–100 | | — | 4500 | — | — | 33,750 | — |
| 3771 | " 101–110 | 24.1 | — | 2750 | — | — | 53,750 | — |
| 3893 | " 111–120 | | | | | | | |
| 3896 | " 121–130 | | | | | | | |
| 3889 | " 131–190 | | | | | | | |

Table 24

In Vitro Folliculotropin Releasing Hormone (FRH)
Activity of Fractions from Carboxymethylcellulose
Chromatography (Stage CMC)

| IBR No. | Description | Wt. of dose, mg | Preincubation | | Incubation (ng FSH/ml) | | | |
|---|---|---|---|---|---|---|---|---|
| | | | $P_1$ | $P_2$ | $I_3$ | $I_4$ | $I_5$ | $I_6$ |
| 3039 | DH-128-A-No. 6 | 0.5,2.6 | 6400 | 4200 | 17,650 | 12,750 | 48,500 | 48,000 |
| 3040 | DH-128-A-No. 7 | 0.5,2.4 | 4000 | 4900 | 12,600 | 23,500 | 80,500 | 92,500 |
| 3041 | DH-128-A-No. 8 | 0.4,2.0 | 2800 | 4350 | 14,550 | 20,000 | 103,500 | 99,000 |
| 3042 | DH-128-A-No. 9 | 0.4,1.8 | 2900 | 3850 | 18,950 | 34,750 | >128,000 | >128,000 |
| 3043 | DH-128-A-No. 10 | 0.2,1.0 | 3100 | 3200 | 4,500 | 4,650 | 8,550 | 9,500 |
| 3062 | DH-128-A-No.61-65 | | 3350 | 3150 | 3,850 | 3,850 | 9,850 | 17,300 |

Table 25

In Vitro FRH Activity of Fractions From Bio-Rad AG-11A8
Ion Retardation Resin (Stage AG)

| IBR No. | Description | Wt. of dose, mg | Preincubation | | Incubation (ng FSH/ml) | | | |
|---|---|---|---|---|---|---|---|---|
| | | | $P_1$ | $P_2$ | $I_3$ | $I_4$ | $I_5$ | $I_6$ |
| 3640 | DH-128-PC-A: 1–20 | 1.0,5.1 | — | 1100 | — | 6700 | 24,850 | — |
| 3461 | DH-128-PC-A: 21–40 | 0.2,1.1 | — | 3000 | — | 2750 | 5,300 | — |
| 3462 | DH-128-PC | | | | | | | |

Table 25-continued

In Vitro FRH Activity of Fractions From Bio-Rad AG-11A8 Ion Retardation Resin (Stage AG)

| IBR No. | Description | Wt. of dose, mg | Preincubation | | Incubation | | | |
|---|---|---|---|---|---|---|---|---|
| | | | $P_1$ | $P_2$ | $I_3$ | $I_4$ | $I_5$ | $I_6$ |
| 3463 | A: 41–70 DH-128-PC- | 0.3,1.6 | — | 1700 | — | 3150 | 2,650 | — |
| 3611 | A: 71–165 DH-128-PC- | 0.4,2.0 | — | 3750 | — | 2300 | 16,350 | — |
| | A: 1M HOAc | 2.0,11.0 | — | 2250 | — | 39,750 | 99,500 | — |

Table 26

In Vitro FRH Activity of Fractions From Diethylaminoethyl cellulose Chromatography (Stage DEAE)

| IBR No. | Description | Wt. of Dose, mg | Preincubation | | Incubation | | | |
|---|---|---|---|---|---|---|---|---|
| | | | $P_1$ | $P_2$ | $I_3$ | $I_4$ | $I_5$ | $I_6$ |
| 3309 | BC-57-2-6–10 | 0.6,3.0 | 1750 | <1000 | 4400 | 3150 | 4350 | 5500 |
| 3310–3317 | BC-57-2-11–70 | 0.2,1.1 | 1860 | 1370 | 2290 | 2540 | 2720 | 1980 |
| 3318–3321 | BC-57-2-71–110 | 0.02,0.12 | 1990 | 1590 | 2050 | 3210 | 2500 | 2750 |
| 3612 | BC-57-2-2 M HOAc | 0.06,0.3 | — | 1500 | — | 17,500 | 66,750 | — |

Table 27

In Vitro Folliculotropin Releasing Hormone (FRH) Activity After Cellulose TLC in Basic and Acidic Solvent Systems (Stage TLC)

| IBR No. | Description | Wt. of dose, mg | Preincubation | | Incubation | | | |
|---|---|---|---|---|---|---|---|---|
| | | | $P_1$ | $P_2$ | $I_3$ | $I_4$ | $I_5$ | $I_6$ |
| | BASIC | | | | | | | |
| 3323 | BC-57-AG-Band 1 | | 1300 | 1300 | 2750 | 1000 | 3000 | 2400 |
| 3324 | BC-57-AG-Band 2 | | 1150 | 1100 | 3000 | 2000 | 2050 | 3000 |
| 3325 | BC-57-AG-Band 3 | 0.4,2.0 | 1100 | 2100 | 5400 | 5750 | 24,500 | 26,200 |
| 3326 | BC-57-AG-Band 4 | | 2100 | 1100 | 2100 | 1500 | 1800 | 3350 |
| 3327 | BC-57-AG-Band 5 | | <1000 | 1050 | 3000 | 2050 | 3800 | 3600 |
| 3328 | BC-57-AG-Band 6 | | 2150 | 1450 | 1100 | 2500 | 3650 | 3400 |
| | ACIDIC | | | | | | | |
| 3704 | "Band 1 | | — | 3300 | — | — | 7500 | — |
| 3705 | "Band 2 | | — | 3300 | — | — | 8500 | — |
| 3706 | "Band 3 | | — | 2350 | — | — | 6500 | — |
| 3707 | "Band 4 | | | | | | | |
| 3708 | "Band 5 | | | | | | | |
| 3709 | "Band 6 | | | | | | | |
| 3710 | "Band 7 | | — | 2000 | — | 14,200 | 42,650 | — |
| 3711 | "Band 8 | | — | 2400 | — | 4350 | 5250 | — |

What is claimed:

1. The new and partially isolated hypothalamic hormone, Folliculotropin Releasing Hormone (FRH), which fulfills the same biological function as the intact hypothalamus of mammalians of releasing folliculotropin and which has an Rf of about 0.4 on cellulose TLC in the solvent system chloroform-methanol-32% acetic acid (60:45:20) and an Rf of about 0.6 on cellulose TLC in the solvent system chloroform-methanol-29% ammonium hydroxide (60:45:20).

2. A method for biosynthetically preparing the Folliculotropin Releasing Hormone (FRH) to provide an increased yield at high purity of said FRH directly from hypothalamic tissue said method comprising lyophilizing incubated hypothalamic tissue and thereafter extracting and defatting said lyophilized tissue to obtain a standard preparation; twice passing said standard preparation through a filtering medium; chromatographing said twice passed preparation a first time on a partition column in a solvent system which is selected from those systems consisting of 0.1% acetic acid in water-n-butanol-pyridine (11-5-3); separating said preparation by means of a linear or step-wise gradient into those components which exhibit LRH and FRH activities; and, chromatographing a second time that separated component which exhibits FRH activity in said solvent system to biosynthetically obtain FRH.

3. A method for diagnosing and analysing fertility in mammals comprising administering to a mammal a biologically effective amount of the FRH hormone of claim 1.

4. The method of claim 2 wherein said method includes identifying said biosynthetically produced FRH by tagging its amino acids with a radioactive substance selected from the group consisting of tritium and carbon-14.

* * * * *